(12) United States Patent
Iwasaki et al.

(10) Patent No.: US 9,894,258 B2
(45) Date of Patent: Feb. 13, 2018

(54) IMAGE PICKUP APPARATUS, AND OPERATION METHOD OF IMAGE PICKUP APPARATUS

(71) Applicant: OLYMPUS CORPORATION, Tokyo (JP)

(72) Inventors: Tomoki Iwasaki, Fuchu (JP); Kazuma Kaneko, Hachioji (JP); Susumu Hashimoto, Hachioji (JP); Yuji Kutsuma, Kokubunji (JP); Soichiro Koshika, Mitaka (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 15/012,050

(22) Filed: Feb. 1, 2016

(65) Prior Publication Data

US 2016/0156822 A1    Jun. 2, 2016

Related U.S. Application Data

(63) Continuation of application No. PCT/JP2014/081832, filed on Dec. 2, 2014.

(30) Foreign Application Priority Data

Dec. 6, 2013  (JP) ................. 2013-253165

(51) Int. Cl.
*H04N 5/00* (2011.01)
*H04N 5/225* (2006.01)
(Continued)

(52) U.S. Cl.
CPC ....... *H04N 5/2256* (2013.01); *A61B 1/00006* (2013.01); *A61B 1/00009* (2013.01);
(Continued)

(58) Field of Classification Search
CPC .................. A61B 1/0638; A61B 11/00009
(Continued)

(56) References Cited

U.S. PATENT DOCUMENTS

| 8,675,046 B2 * | 3/2014 | Kubo ................. A61B 1/00009 348/42 |
| 2007/0040906 A1 * | 2/2007 | Iketani ................. A61B 1/0638 348/69 |

(Continued)

FOREIGN PATENT DOCUMENTS

| EP | 2537456 A1 | 12/2012 |
| JP | 2005-218647 A | 8/2005 |

(Continued)

OTHER PUBLICATIONS

International Search Report dated Mar. 10, 2015 issued in PCT/JP2014/081832.

*Primary Examiner* — Dave Czekaj
*Assistant Examiner* — Shanika Brumfield
(74) *Attorney, Agent, or Firm* — Scully, Scott, Murphy & Presser, P.C.

(57) ABSTRACT

An image pickup apparatus includes a light source apparatus emitting a first or a second illumination light to an object, an image pickup device acquiring an image of the object, and a CPU switching between a first mode where the image is picked up with the first illumination light and a second mode where the image is picked up with the second illumination light, being able to set at least one of a processing parameter for processing an image and a brightness control parameter before switching the illumination light to the illumination light corresponding to the mode or after switching to the corresponding illumination light is completed, and controlling whether the processing parameter is set before switching of the illumination light is started or after switching is
(Continued)

completed according to the mode switching from the first to the second mode or from the second to the first mode.

5 Claims, 17 Drawing Sheets

(51) Int. Cl.
    *G02B 23/24*     (2006.01)
    *A61B 1/00*     (2006.01)
    *A61B 1/06*     (2006.01)
    *A61B 1/04*     (2006.01)
    *H04N 5/232*     (2006.01)

(52) U.S. Cl.
    CPC .............. *A61B 1/04* (2013.01); *A61B 1/0638* (2013.01); *A61B 1/0661* (2013.01); *G02B 23/2461* (2013.01); *H04N 5/23245* (2013.01); *A61B 1/0646* (2013.01); *H04N 2005/2255* (2013.01)

(58) Field of Classification Search
    USPC .......................................................... 348/68
    See application file for complete search history.

(56) References Cited

U.S. PATENT DOCUMENTS

| | | | |
|---|---|---|---|
| 2008/0306343 A1* | 12/2008 | Yamazaki | A61B 1/00009 600/180 |
| 2010/0141747 A1* | 6/2010 | Kubo | A61B 1/00009 348/68 |
| 2012/0215066 A1 | 8/2012 | Akiyama et al. | |
| 2013/0286175 A1* | 10/2013 | Hashimoto | A61B 1/0638 348/68 |

FOREIGN PATENT DOCUMENTS

| | | |
|---|---|---|
| JP | 2009-148487 A | 7/2009 |
| JP | 2012-223349 A | 11/2012 |
| JP | 5076036 B2 | 11/2012 |
| WO | WO 2011/162111 A | 12/2011 |

* cited by examiner

IMAGE PICKUP APPARATUS, AND OPERATION METHOD OF IMAGE PICKUP APPARATUS

CROSS REFERENCE TO RELATED APPLICATION

This application is a continuation application of PCT/JP2014/081832 filed on Dec. 2, 2014 and claims benefit of Japanese Application No. 2013-253165 filed in Japan on Dec. 6, 2013, the entire contents of which are incorporated herein by this reference.

BACKGROUND OF INVENTION

1. Field of the Invention

The present invention relates to an image pickup apparatus whose mode can transition among a plurality of modes with different light emission amounts of an illumination light, and an operation method of the image pickup apparatus.

2. Description of the Related Art

Conventionally, an image pickup apparatus such as an endoscope is known, which has a plurality of observation modes with different light amounts of an illumination light to be emitted to an object, and which observes an object while switching these observation modes.

The plurality of observation modes with different light amounts of an illumination light in the endoscope can specifically include a white light observation (white light imaging: WLI) mode in which a white light is emitted to an object, a narrow band observation (narrow band imaging: NBI) mode in which a narrow band light is emitted. Here, while, in the white light observation mode, almost all the light amount which can be emitted by a light source can be employed as an illumination light, in the narrow band observation mode, because only part of the light amount which can be emitted by a light source can be employed, the light amount of an illumination light which can be emitted in the narrow band light observation mode is relatively smaller than the light amount of the illumination light which can be emitted in the white light observation mode. These observation modes are modes for performing observation according to purpose by not only having different absolute light emission amounts, but also making wavelength bands of the illumination light different.

Specifically, in such an image pickup apparatus, a wavelength changing unit such as a filter is provided at a light source apparatus, so that illumination lights with different light amounts and different wavelength bands are radiated.

For example, Japanese Patent Application Laid-Open Publication No. 2009-148487 discloses a technique of, in a light source apparatus in which a plurality of filters for changing a wavelength of a light emitted from a xenon lamp can be disposed on an optical path of the emission light, and an endoscope apparatus, improving response at switching of an observation mode by stopping control of a light amount during operation for changing the wavelength.

According to such a technique, it is possible to reduce brightness disorder of an image during switching of the observation mode. By the way, when the observation mode is switched among a plurality of observation modes, it is necessary to switch setting of an image processing parameter for processing the obtained image, in addition to simply inserting or removing a filter on an optical path of the illumination light. When the image processing parameter is switched, color tone of the image changes.

SUMMARY OF THE INVENTION

An image pickup apparatus according to one aspect of the present invention includes a light source unit provided so as to be able to emit a first illumination light or a second illumination light which has a relatively smaller light emission amount than a light emission amount of the first illumination light to an object, an image acquiring unit configured to acquire an image by picking up an image of the object illuminated with the first illumination light or the second illumination light, a mode switching unit configured to switch a mode from one of a first mode in which the image is picked up by illuminating the object with the first illumination light and a second mode in which the image is picked up by illuminating the object with the second illumination light, to the other mode, a parameter setting unit configured to be able to set at least one of a processing parameter for processing the image acquired by the image acquiring unit in a mode after the mode is switched and a brightness control parameter for controlling intensity of the illumination light emitted from the light source unit before the illumination light emitted from the light source unit is switched to an illumination light corresponding to the mode after the mode is switched or after switching to the illumination light corresponding to the mode after the mode is switched is completed by the mode switching unit, and a control unit configured to control whether the processing parameter by the parameter setting unit is set before switching to the illumination light corresponding to the mode after the mode is switched is started or after switching to the illumination light corresponding to the mode after the mode is switched is completed according to whether the mode is switched by the mode switching unit from the first mode to the second mode or from the second mode to the first mode.

An operation method of an image pickup apparatus according to one aspect of the present invention includes an illumination step of a light source unit emitting a first illumination light or a second illumination light which has a relatively smaller light emission amount than a light emission amount of the first illumination light to an object, an image acquiring step of an image acquiring unit acquiring an image by picking up an image of the object illuminated with the first illumination light or the second illumination light, a mode switching step of a mode switching unit switching a mode from one of a first mode in which the image is picked up by illuminating the object with the first illumination light and a second mode in which the image is picked up by illuminating the object with the second illumination light, to the other mode, a parameter setting step of a parameter setting unit setting at least one of a processing parameter for processing the image acquired in the image acquiring step in a mode after the mode is switched and a brightness control parameter for controlling intensity of the illumination light emitted in the illumination step before the illumination light emitted from the light source unit is switched to an illumination light corresponding to the mode after the mode is switched or after switching to the illumination light corresponding to the mode after the mode is switched is completed in the mode switching step, and a control step of a control unit controlling whether the processing parameter in the parameter setting step is set before switching to the illumination light corresponding to the mode after the mode is switched is started or after switching to the illumination light corresponding to the mode after the mode is switched is completed according to whether the mode is switched in the mode switching step from the first mode to the second mode or from the second mode to the first mode.

DETAILED DESCRIPTION OF THE PREFERRED EMBODIMENT(S)

Embodiments of the present invention will be described below with reference to the drawings.

Embodiment 1

Figure 1:
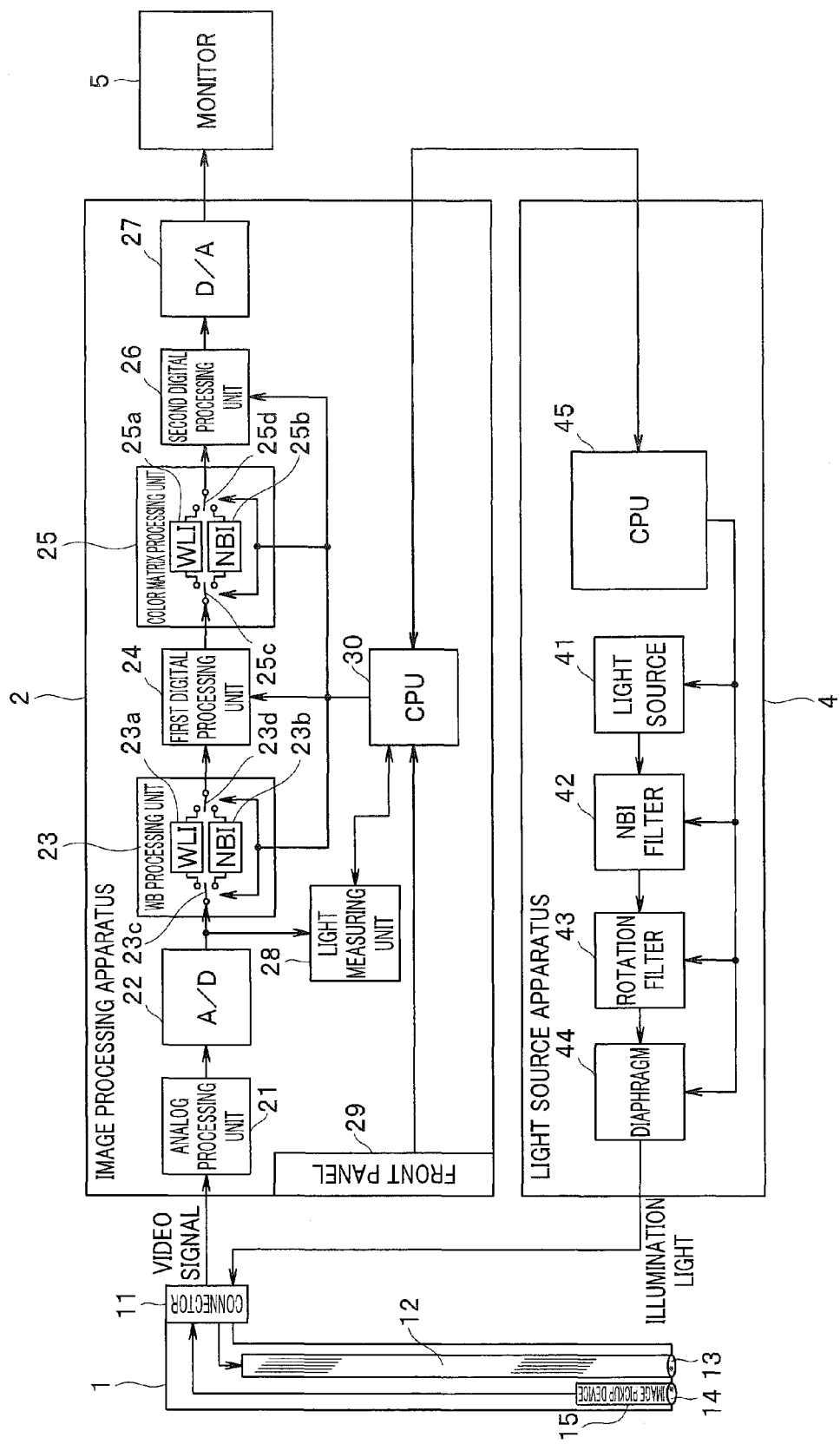
FIG. 1 is a block diagram illustrating a configuration of an endoscope system to which an image pickup apparatus is applied in Embodiment 1 of the present invention.

FIG. 1 to FIG. 4 illustrate Embodiment 1 of the present invention, and FIG. 1 is a block diagram illustrating a configuration of an endoscope system to which an image pickup apparatus is applied.

The endoscope system, which is directed to observation an object (also referred to as a subject in the field of an endoscope) in the dark, is an electronic endoscope system including an endoscope 1, an image processing apparatus 2, a light source apparatus 4 and a monitor 5.

The endoscope 1 includes a connector 11, a light guide 12, an illumination optical system 13, an image forming optical system 14 and an image pickup device 15.

The connector 11 connects the endoscope 1 to the image processing apparatus 2 and the light source apparatus 4.

The light guide 12 transmits an illumination light supplied from the light source apparatus 4 to a distal end side of an insertion portion of the endoscope 1.

The illumination optical system 13 illuminates the object in the dark with the illumination light transmitted from the light guide 12 from the distal end of the insertion portion of the endoscope 1.

The image forming optical system 14 forms an optical image of the object.

The image pickup device 15 is an image acquiring unit configured to acquire an image by picking up the optical image formed by the image forming optical system 14, of the object illuminated with a first illumination light (white light in the present embodiment) or a second illumination light (narrow band light in the present embodiment) which will be described later, and output the image as a video signal. The image outputted from the image pickup device 15 is transmitted to the image processing apparatus 2 via the connector 11.

The image processing apparatus 2 which controls and drives the endoscope 1 and processes the image obtained from the endoscope 1, includes an analog processing unit 21, an A/D converting unit 22, a WB (white balance) processing unit 23, a first digital processing unit 24, a color matrix processing unit 25, a second digital processing unit 26, a D/A converting unit 27, a light measuring unit 28, a front panel 29 and a CPU 30.

The analog processing unit 21 reduces noise by performing correlative double sampling (CDS) on the image outputted from the image pickup device 15.

The A/D converting unit 22 converts the analog signal outputted from the analog processing unit 21 into a digital signal.

The WB processing unit 23 includes a WLI-WB processing unit 23a configured to perform white balance processing for a white light observation (white light imaging: WLI) mode which is the first mode, an NBI-WB processing unit 23b configured to perform white balance processing for a narrow band observation (narrow band imaging: NBI) mode which is the second mode, an input side selection switch 23c and an output side selection switch 23d.

The WLI-WB processing unit 23a performs white balance processing on the image to be displayed on the monitor 5 in the WLI mode in which the light source apparatus 4 emits a white light (first illumination light).

The NBI-WB processing unit 23b performs white balance processing on the image to be displayed on the monitor 5 in the NBI mode in which the light source apparatus 4 emits a narrow band light (second illumination light).

The input side selection switch 23c and the output side selection switch 23d are configured to be able to be switched in conjunction with each other based on control by the CPU 30, and, when the observation mode is set at the WLI mode, the input side selection switch 23c is switched so that input is performed to the WLI-WB processing unit 23a and the output side selection switch 23d is switched so that output is performed from the WLI-WB processing unit 23a, while, when the observation mode is set at the NBI mode, the input side selection switch 23c is switched so that input is performed to the NBI-WB processing unit 23b and the output side selection switch 23d is switched so that output is performed from the NBI-WB processing unit 23b.

The first digital processing unit 24 performs image processing such as synchronization processing on the image outputted from the WB processing unit 23. The image processing performed by the first digital processing unit 24 includes processing of signal amplification based on a gain set by the CPU 30 (part of a function of AGC (auto gain control)) according to whether the observation mode is the WLI mode or the NBI mode.

The color matrix processing unit 25 includes a WLI-color matrix processing unit 25a configured to perform color matrix processing for the WLI mode, an NBI-color matrix processing unit 25b configured to perform color matrix processing for the NBI mode, an input side selection switch 25c and an output side selection switch 25d.

The WLI-color matrix processing unit 25a performs color matrix processing on an image in the WLI mode, while the NBI-color matrix processing unit 25b performs color matrix processing on an image in the NBI mode.

The input side selection switch 25c and the output side selection switch 25d are configured to be able to be switched in conjunction with each other based on control by the CPU 30 as with each switch in the WB processing unit 23, and, the switches are switched in the WLI mode so that input/output is performed to/from the WLI-color matrix processing unit 25a, while the switches are switched in the NBI mode so that input/output is performed to/from the NBI-color matrix processing unit 25b.

The second digital processing unit 26 performs various kinds of image processing such as γ conversion, on the image processed by the color matrix processing unit 25.

The D/A converting unit 27 converts the digital image signal processed by the second digital processing unit 26 into an analog image signal and outputs the analog image signal to the monitor 5.

The light measuring unit 28 calculates brightness of the image acquired by the image pickup device 15 and converted into a digital signal by the A/D converting unit 22 at predetermined calculation frequency, and outputs the measured light measurement value to the CPU 30. Note that the calculation frequency in the light measuring unit 28 can be changed by setting from the CPU 30.

The front panel 29 is a user interface configured to perform input operation to the image processing apparatus 2 or the whole endoscope system, display of a system state, or the like.

The CPU 30 is a control unit configured to control the image processing apparatus 2, and, further, the whole endoscope system including the endoscope 1 and the light source apparatus 4.

That is, the CPU 30 functions as a mode transitioning unit which makes the mode transition from one of the WLI mode (first mode) in which an image is picked up by illuminating the object with the white light (first illumination light) and the NBI mode (second mode) in which an image is picked up by illuminating the object with the narrow band light (second illumination light) to the other mode.

Further, the CPU 30 also functions as a parameter setting unit which, after transition of the mode is completed by the function as the mode transitioning unit, sets at least one of a processing parameter for processing the image acquired by the image pickup device 15 in a mode after the mode transitions and a brightness control parameter for controlling intensity of the illumination light emitted from the light source apparatus 4.

Still further, the CPU 30 can set a processing parameter for processing the image in the mode after the mode transitions before transition of the mode is completed, and also functions as a parameter setting timing control unit configured to control a timing for setting the processing parameter according to whether the mode transitions from the WLI mode to the NBI mode or from the NBI mode to the WLI mode (specifically, see FIG. 3 and FIG. 4 which will be described later).

Further, as part of a function of AGC, the CPU 30 sets a gain according to the light measurement value obtained by the light measuring unit 28 and whether the observation mode is the WLI mode or the NBI mode, transmits the set gain to the first digital processing unit 24 and makes the first digital processing unit 24 amplify the image signal.

The light source apparatus 4 is a light source unit provided so as to be able to emit a white light (WLI light) which is the first illumination light or a narrow band light (NBI light) which is the second illumination light which has a relatively smaller light emission amount than a light emission amount of the white light to the object. The light source apparatus 4 emits the first illumination light or the second illumination light to the object in an illumination step.

The light source apparatus 4 supplies the illumination light to be radiated on the object in the dark while, for example, being capable of changing the light amount, and includes a light source 41, an NBI filter 42, a rotation filter 43, a diaphragm 44 and a CPU 45.

The light source 41 is configured to include, for example, a lamp such as a halogen lamp, a xenon lamp and a metal halide lamp, or a semiconductor light emitting device such as an LED. Note that, for example, a light amount of an illumination light is controlled by current control when the light source 41 is a lamp, and controlled by pulse width control (what is called, PWM) when the light source 41 is the semiconductor light emitting device.

The NBI filter 42 which is an optical filter configured to limit a band of a light emitted from the light source 41 to a narrow band light for NBI observation, is inserted on an optical path of the emission light in the NBI mode and retracted from the optical path of the emission light in the WLI mode.

The rotation filter 43 is a rotary filter in which bandpass filters of R (red), G (green) and B (blue) are disposed in a circumferential direction of a turret to convert the illumination light from the light source 41 into a frame-sequential light. By rotating the rotation filter 43, an R light, a G light and a B light are radiated in a time series.

The diaphragm 44 is a light amount diaphragm configured to control a light amount of the illumination light by changing an opening radius through which a light passes. The illumination light emitted from the light source 41 and whose light amount is made a predetermined light amount via the diaphragm 44 in this manner is incident on an incident end of the light guide 12 via the connector 11.

The CPU 45 adjusts the light emission amount of the light source 41 according to control by the CPU 30 based on the light measurement value and adjusts the opening radius of the diaphragm 44. Therefore, the light emission amount from the light source apparatus 4 is adjusted as feedback control based on the light measurement value. Further, the CPU 45 controls the NBI filter 42 and the rotation filter 43 according to whether the set observation mode is the WLI mode or the NBI mode.

The monitor 5 is a display apparatus configured to display the image signal outputted from the image processing apparatus 2.

Figure 2:
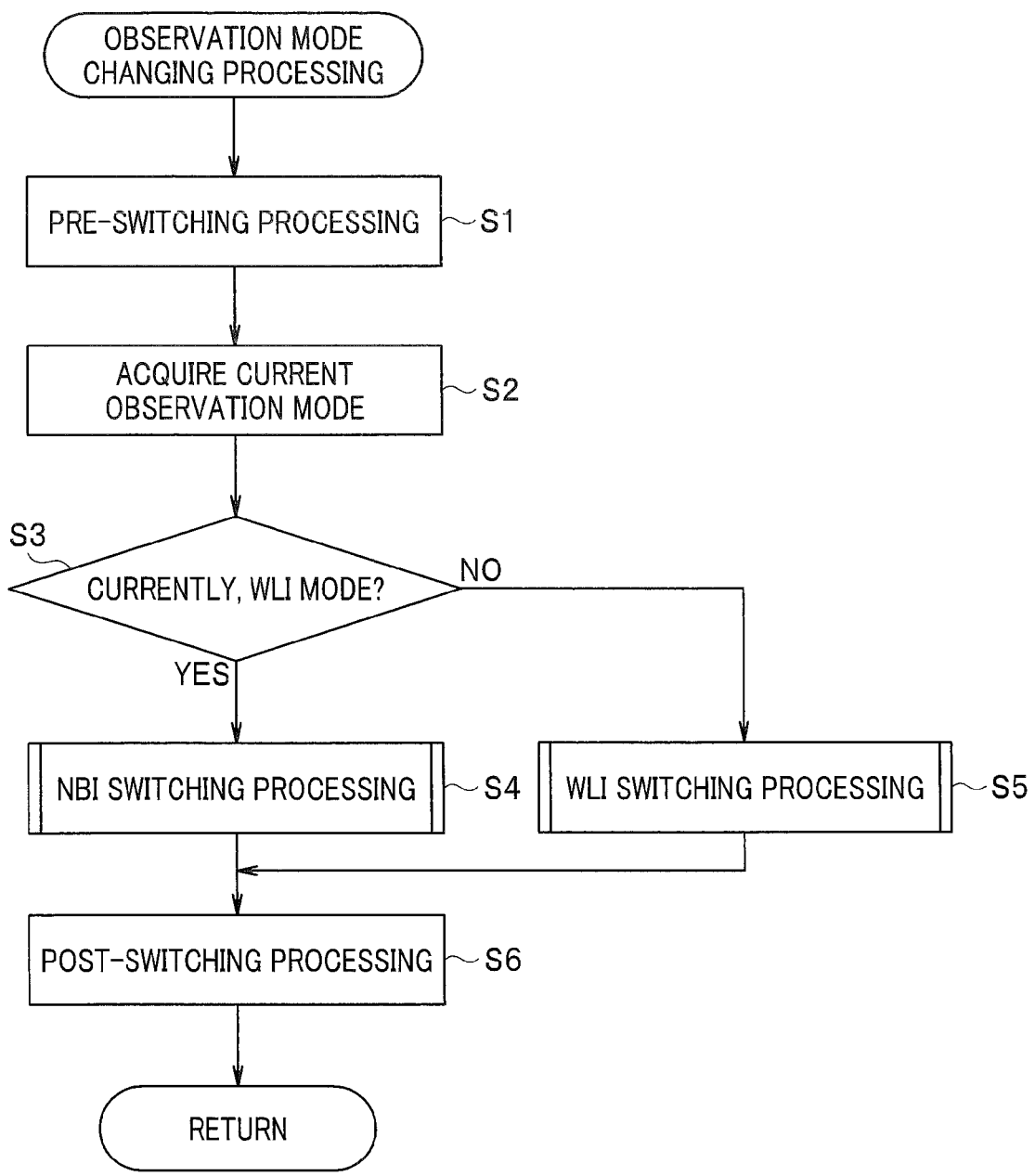
FIG. 2 is a flowchart illustrating an observation mode change processing in the endoscope system in Embodiment 1.

Next, FIG. 2 is a flowchart illustrating an observation mode changing processing in the endoscope system.

When the processing is started, a pre-switching processing is performed which is preparation for switching the observation mode, such as start of energization of a drive source for driving the NBI filter 42 and the rotation filter 43 (step S1).

Then, a current observation mode is acquired (step S2), and it is judged whether the current observation mode is the WLI mode or the NBI mode (step S3).

Here, when it is judged that the current observation mode is the WLI mode, an NBI switching processing for switching the mode to the NBI mode is performed (step S4), while when it is judged that the current observation mode is the NBI mode, a WLI switching processing for switching the mode to the WLI mode is performed (step S5).

When the processing of step S4 or step S5 is finished, a post-switching processing after the observation mode is switched is performed, such as stop of energization to the drive source for driving the NBI filter 42 and the rotation filter 43 as necessary (step S6), and the processing is finished.

Figure 3:
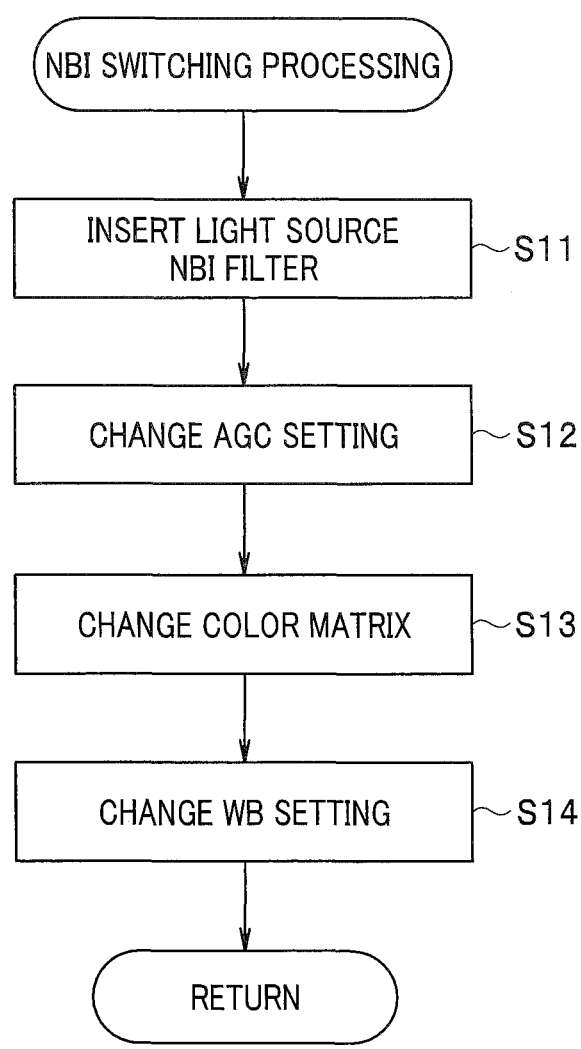
FIG. 3 is a flowchart illustrating details of an NBI switching processing in step S4 in FIG. 2 in Embodiment 1.

FIG. 3 is a flowchart illustrating details of the NBI switching processing in step S4 in FIG. 2.

When the processing is started, the CPU 45 inserts the NBI filter 42 of the light source apparatus 4 into an optical path of the illumination light emitted from the light source 41 based on control by the CPU 30 which functions as the mode transitioning unit (step S11). By this means, transition of the mode by the mode transitioning unit is completed.

Subsequently, the CPU 30 changes setting of the AGC from setting in the WLI mode to setting in the NBI mode (step S12), switches the input side selection switch 25c and the output side selection switch 25d of the color matrix processing unit 25 from the WLI-color matrix processing unit 25a to the NBI-color matrix processing unit 25b (step S13), switches the input side selection switch 23c and the output side selection switch 23d of the WB processing unit 23 from the WLI-WB processing unit 23a to the NBI-WB processing unit 23b (step S14), and returns from this processing.

The CPU 30 which functions as the parameter setting timing control unit in this manner controls a timing for adjusting the processing parameter so as to set processing parameters (processing parameters for AGC, the color matrix processing unit 25, the WB processing unit 23, and the like) for processing the image in the NBI mode after transition from the WLI mode to the NBI mode is completed in the case of the WLI switching processing in which the mode transitions from the WLI mode to the NBI mode.

Figure 4:
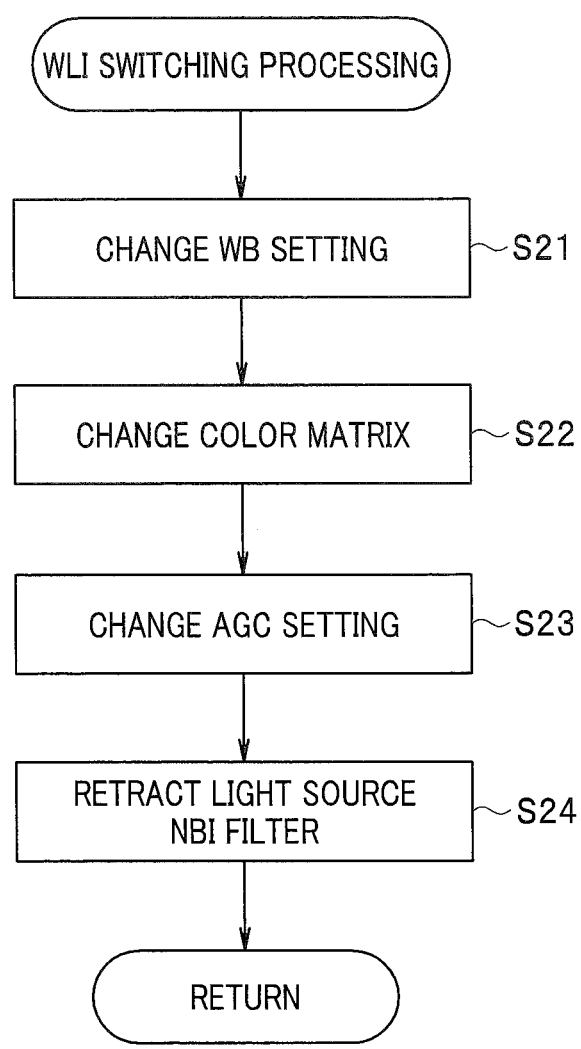
FIG. 4 is a flowchart illustrating details of a WLI switching processing in step S5 in FIG. 2 in Embodiment 1.

FIG. 4 is a flowchart illustrating details of the WLI switching processing in step S5 in FIG. 2.

When this processing is started, the CPU 30 switches the input side selection switch 23c and the output side selection switch 23d of the WB processing unit 23 from the NBI-WB processing unit 23b to the WLI-WB processing unit 23a (step S21), switches the input side selection switch 25c and the output side selection switch 25d of the color matrix processing unit 25 from the NBI-color matrix processing unit 25b to the WLI-color matrix processing unit 25a (step S22), and changes setting of the AGC from setting in the NBI mode to setting in the WLI mode (step S23).

Then, the CPU 45 retracts the NBI filter 42 of the light source apparatus 4 from the optical path of the illumination light emitted from the light source 41 based on control by the CPU 30 which functions as the mode transitioning unit (step S24). By this means, transition of the mode by the mode transitioning unit is completed. Subsequently, the processing returns from this processing.

The CPU 30 which functions as the parameter setting timing control unit in this manner controls a timing for adjusting the processing parameter so as to set processing parameters (processing parameters for AGC, the color matrix processing unit 25, the WB processing unit 23, and the like) for processing the image in the WLI mode before the mode transitions from the NBI mode to the WLI mode in the case of the NBI switching processing in which the mode transitions from the NBI mode to the WLI mode.

According to Embodiment 1, when the mode transitions from the WLI mode to the NBI mode, because the processing parameter for processing an image is changed after the NBI filter 42 is inserted on the optical path, the processing parameter is changed under the NBI light through which a darker image is obtained instead of under the WLI light through which a bright image is obtained, so that it is possible to make color disorder of the image less noticeable.

Further, when the mode is switched from the NBI mode to the WLI mode, because the processing parameter for processing an image is changed before the NBI filter 42 is retracted from the optical path, the processing parameter is changed under the NBI light through which a darker image is obtained instead of under the WLI light through which a bright image is obtained, so that it is possible to make color disorder of the image less noticeable.

In this manner, it is possible to reduce color disorder of an image when the observation mode is switched.

Embodiment 2

Figure 5:
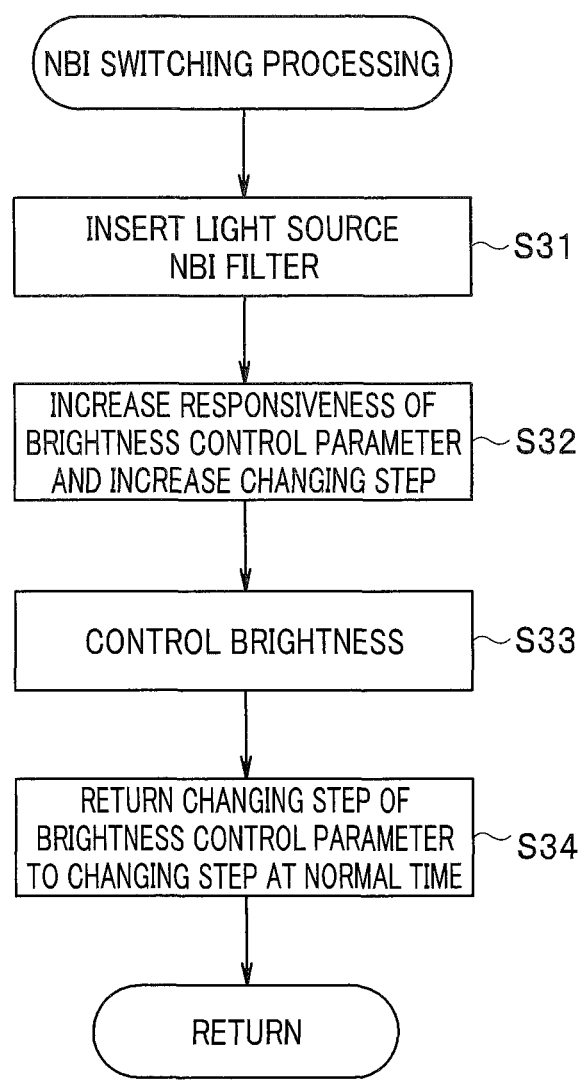
FIG. 5 is a flowchart illustrating details of an NBI switching processing in Embodiment 2 of the present invention.

FIG. 5 to FIG. 8 illustrate Embodiment 2 of the present invention, and FIG. 5 is a flowchart illustrating details of the NBI switching processing.

In Embodiment 2, the same reference numerals are assigned to components which are the same as those in the above-described Embodiment 1, explanation will be omitted as appropriate, and different points will be mainly described.

While, in the above-described Embodiment 1, color disorder of an image when the observation mode is switched is reduced, in Embodiment 2, disorder of brightness of an image after the observation mode is switched is reduced.

During operation in the NBI mode or during operation in the WLI mode, brightness of an image is adjusted by adjusting an exposure time period of the image pickup device 15 and adjusting a gain of the first digital processing unit 24 based on control by the CPU 30 which obtains the light measurement value from the light measuring unit 28, by adjusting a light emission amount of the light source 41 by the CPU 45 through the above-described current control and pulse width control, and by adjusting the opening radius of the diaphragm 44 by the CPU 45. Therefore, examples of the brightness control parameter can include a current value to be supplied to the light source 41, a pulse width in PWM in the case where the light source 41 is a semiconductor light emitting device such as an LED, an exposure time period of the image pickup device 15, a gain of the image obtained through image pickup by the image pickup device 15, and calculation frequency at the light measuring unit 28.

At this time, the CPU 30 adjusts brightness based on the light measurement value obtained by the light measuring unit 28 so that brightness of the image displayed on the monitor 5 gets closer to predetermined brightness.

Here, if a time interval for adjusting brightness of the image is set too short (that is, response of adjustment is set too fast), or an adjustment width for adjusting the brightness of the image is set too large, it may be a cause of hunting which is unstable fluctuation of the brightness of the image within a short time period. Therefore, the CPU 30 which functions as a parameter setting unit adjusts and sets the brightness control parameter for controlling the brightness of the image for each predetermined unit time period in units of a changing step of a predetermined step width, so that the unit time period and the changing step are controlled to be a level which does not cause hunting. Accordingly, for example, when a change width for which it is desired to adjust brightness is larger than the step width of the changing step, it takes a plurality of unit time periods to adjust brightness so that the brightness asymptotically gets closer to target brightness.

In contrast to this, a change amount of the brightness of the image when the observation mode is switched is dramatically larger than a change amount of the brightness of the image during operation in the NBI mode or during operation in the WLI mode, and it requires a long time period to reach appropriate brightness of the image through normal brightness adjustment control, and until the brightness reaches the appropriate brightness, an image with inappropriate brightness is observed.

Therefore, in the present embodiment, a time interval for adjusting the brightness of the image when the observation mode is switched is set shorter than a time interval at a normal time, and an adjustment width for adjusting the brightness of the image is set larger than an adjustment width at the normal time.

In the present embodiment, each processing performed in step S4 and step S5 in FIG. 2 in the above-described Embodiment 1 will be described with reference to FIG. 7 and FIG. 8 along FIG. 5 and FIG. 6.

When the NBI switching processing illustrated in FIG. 5 is started, the CPU 45 inserts the NBI filter 42 of the light source apparatus 4 on the optical path of the illumination light emitted from the light source 41 based on control by the CPU 30 which functions as the mode transitioning unit (step S31). By this means, transition of the mode by the mode transitioning unit is completed.

The CPU 30 then increases responsiveness of the brightness control parameter for controlling intensity of the illumination light emitted from the light source apparatus 4 and increases the changing step (step S32), and controls brightness of the image based on the increased brightness control parameter (step S33).

Subsequently, after a predetermined time period has elapsed, a changing step of the brightness control parameter is returned to a changing step at a normal time (step S34), and the processing is returned from this processing.

Figure 7:
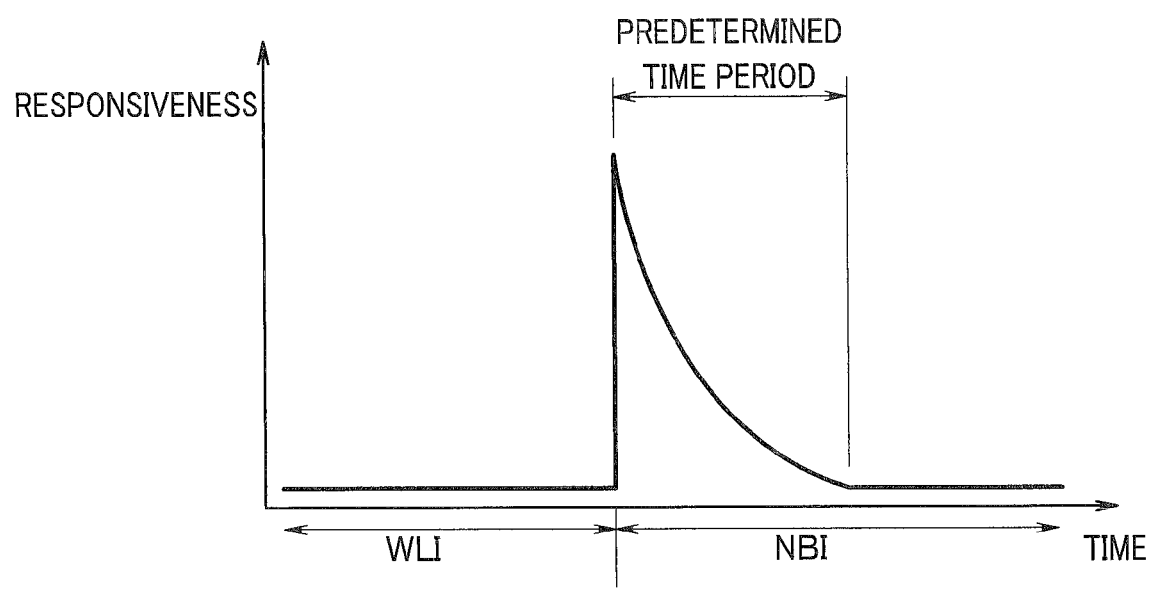
FIG. 7 is a line map illustrating aspect of change of responsiveness in the NBI switching processing in Embodiment 2.
Figure 8:
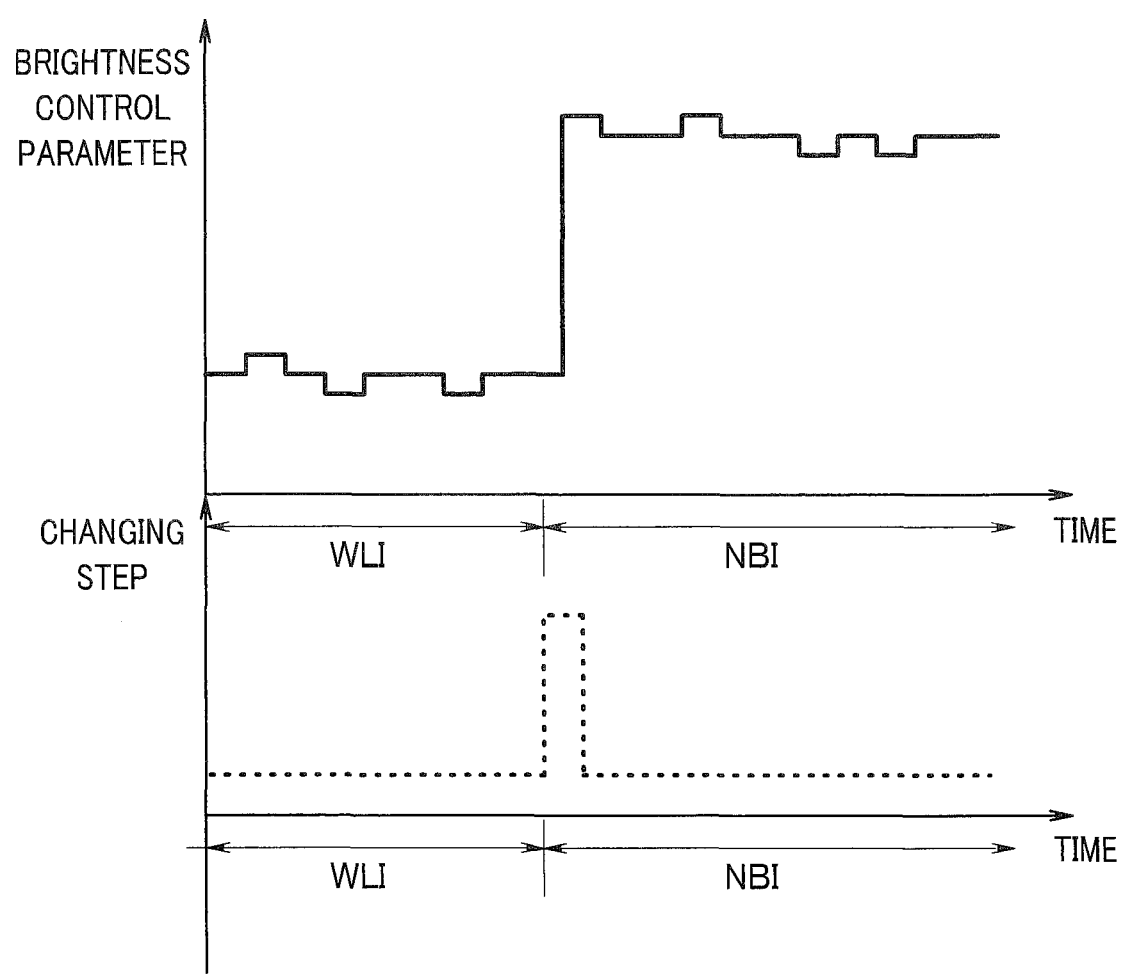
FIG. 8 is a line map illustrating aspect of change of a changing step in the NBI switching processing in Embodiment 2.

Here, FIG. 7 is a line map illustrating aspect of change of responsiveness in the NBI switching processing, and FIG. 8 is a line map illustrating aspect of change of the changing step in the NBI switching processing.

As illustrated in FIG. 7, while responsiveness of brightness control which is a parameter (one of the brightness control parameters) for setting calculation frequency at the light measuring unit 28 is controlled to be a fixed low level to some extent at the normal time to prevent hunting, or the like, the level is raised so that calculation frequency becomes higher than calculation frequency before the mode transitions (normal time) within a predetermined time period after transition of the mode from the WLI mode to the NBI mode is completed, and returned to the fixed level at the normal time again after the predetermined time period has elapsed.

At this time, responsiveness within the predetermined time period may be a fixed high level, or, as illustrated in FIG. 7, the responsiveness may be reduced so as to be asymptotically returned to be the fixed level at the normal time.

Further, as indicated in a dotted line graph in a lower part of FIG. 8, the CPU 30 which functions as a parameter setting unit controls a changing step which is a unit for changing the brightness control parameter to a fixed level so that change of brightness does not become extremely large at the normal time.

In contrast to this, because brightness of the image largely changes when the observation mode transitions, it takes time until brightness of the image becomes stable only with the same control as that performed at the normal time. Therefore, within a predetermined time period immediately after transitioning of the observation mode is completed, a larger step width is set regardless of limitation of a step width at the normal time.

Specifically, within a predetermined period immediately after transition from the WLI mode to the NBI mode is completed as illustrated in FIG. 8, the CPU 30 sets the changing step larger (higher level) than the changing step at the normal time. Then, immediately after that, the CPU 30 returns the changing step to the fixed level at the normal time.

Therefore, the level of the changing step within the predetermined time period immediately after transition of the mode is completed is preferably a level corresponding to change amounts of brightness of the image in the WLI mode and brightness of the image in the NBI mode. As a result of this, as indicated in a solid line graph in an upper part of FIG. 8, within a predetermined time period immediately after transition of the mode is completed, a value of the brightness control parameter in the WLI mode is substantially instantaneously changed to a value of the brightness control parameter in the NBI mode. By this means, it is possible to observe an image of brightness suitable for the NBI mode from a moment the NBI mode is started without the brightness control parameter in the WLI mode being used in the NBI mode.

However, while the brightness control parameter is changed from the WLI mode to the NBI mode in one step in the example illustrated in FIG. 8, if the number of steps can be reduced compared to a case where the brightness control parameter is changed in the changing step at the normal time, the brightness control parameter may be changed over a plurality of steps. Also in this case, it is possible to reach an image of brightness suitable for the NBI mode within a shorter time period.

Figure 6:
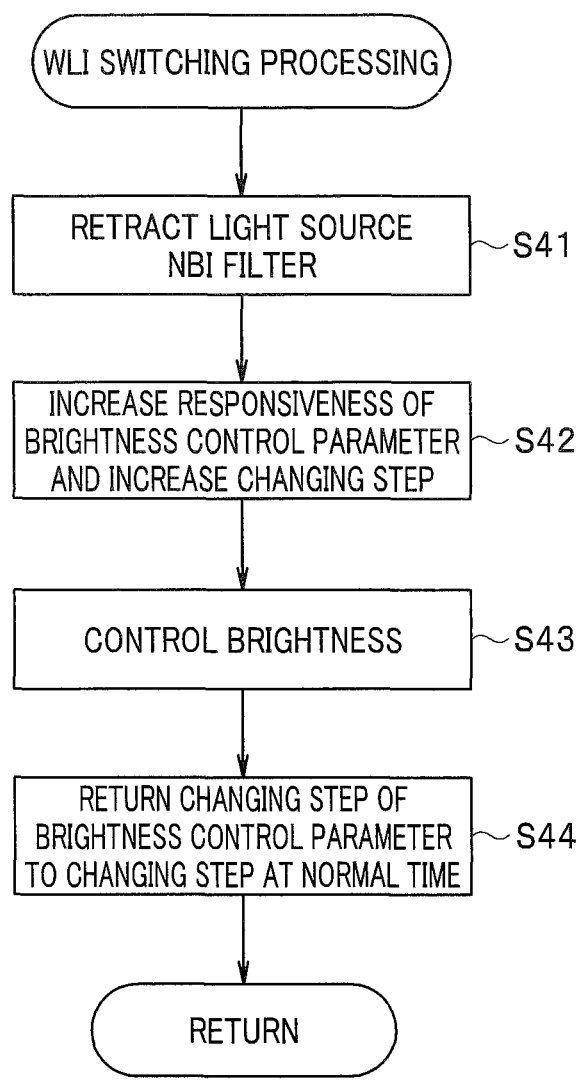
FIG. 6 is a flowchart illustrating details of a WLI switching processing in Embodiment 2.

Next, FIG. 6 is a flowchart illustrating details of the WLI switching processing in the present embodiment.

When the processing is started, the CPU 45 retracts the NBI filter 42 of the light source apparatus 4 from the optical path of the illumination light emitted from the light source 41 based on control by the CPU 30 which functions as the mode transitioning unit (step S41). By this means, transition of the mode by the mode transitioning unit is completed.

The CPU 30 then increases responsiveness of the brightness control parameter for controlling intensity of the illumination light emitted from the light source apparatus 4 and increases the changing step (step S42), and controls brightness of the image based on the increased brightness control parameter (step S43).

Subsequently, after a predetermined time period has elapsed, the changing step of the brightness control parameter is returned to the changing step at the normal time (step S44), and the processing is returned from this processing.

Note that while FIG. 7 and FIG. 8 illustrate examples of the responsiveness and the changing step of the brightness control parameter at the NBI switching processing (when the mode is switched from the WLI mode to the NBI mode), in a similar manner, at the WLI switching processing (when the mode is switched from the NBI mode to the WLI mode), the responsiveness is increased only for a predetermined time period, and the level of the changing step is set larger within the predetermined time period immediately after transition of the mode is completed.

According to Embodiment 2, when the mode is switched from the WLI mode to the NBI mode, or from the NBI mode to the WLI mode, because the changing step is increased while increasing the responsiveness of the brightness control parameter, it is possible to reduce disorder of the brightness of the image immediately after the observation mode is switched.

Further, within the predetermined time period, while response within a short time period is made possible by making the responsiveness which is increased once asymptotically closer to the responsiveness at the normal time, it is possible to effectively reduce hunting.

Note that while, in the above-described embodiments, the first illumination light is a white light and the second illumination light is a narrow band light, the present invention is not limited to this, and out of two types of illumination lights with relatively different light emission amounts, if a light with a larger light emission amount is set as the first illumination light, and a light with a smaller light emission amount is set as the second illumination light, it is possible to apply the present invention to arbitrary illumination lights.

Related Explanation of Each Embodiment

By the way, because of a semiconductor structure (a structure on which a thin film of a metal, a silicon, a contact, or the like, are formed) of the image pickup device such as a CCD, or for other electrical reasons, there is a case where periodic change (for example, periodic luminance change forming a striped pattern) occurs in an image signal obtained through photoelectric conversion. For example, when there is sensitivity variation in a silicon portion which is a light receiving face of the image pickup device, there is a case where periodic signal value fluctuation depending on a wavelength of an incident light may occur. A technique for reducing periodic noise (what is called fixed pattern noise) specific to such an image pickup device will be described with reference to FIG. 9 to FIG. 14.

Figure 9:
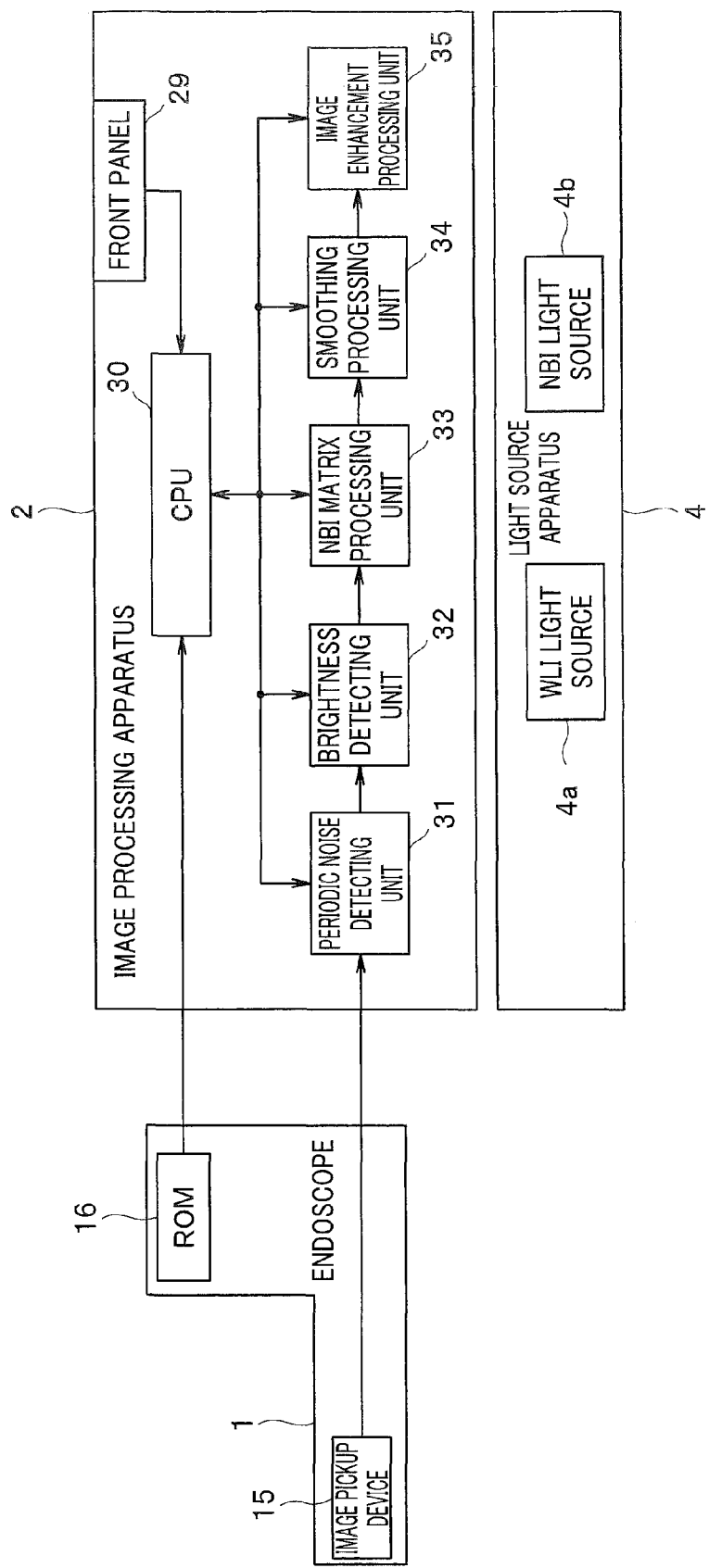
FIG. 9 is a block diagram illustrating a configuration of an endoscope system to which an image pickup apparatus is applied according to the above-described embodiments.

FIG. 9 is a block diagram illustrating a configuration of an endoscope system to which the image pickup apparatus is applied.

The endoscope system includes an endoscope 1, an image processing apparatus 2 and a light source apparatus 4, and is an electric endoscope system also including a monitor, or the like, which is not illustrated.

The endoscope 1 includes an image pickup device 15 and a ROM 16.

The image pickup device 15 which is an image acquiring unit configured to pick up an optical image of the object to acquire an image and output the image as a video signal, is configured as, for example, a CCD.

The ROM 16 which is a storage medium configured to store scope information relating to the endoscope 1 in a non-volatile manner, also stores periodic noise information of the image pickup device 15. Here, the periodic noise information includes a noise direction (a direction the striped pattern is arranged) and a noise cycle (a space cycle (space length) the striped pattern is arranged) of the periodic noise.

The image processing apparatus 2 which controls and drives the endoscope 1 and processes the image obtained from the endoscope 1, includes a front panel 29, a CPU 30, a periodic noise detecting unit 31, a brightness detecting unit 32, an NBI matrix processing unit 33, a smoothing processing unit 34 and an image enhancement processing unit 35.

The front panel 29 is a user interface configured to perform input operation to the image processing apparatus 2 or the whole endoscope system, display of the system state, or the like. It is possible to set on/off of periodic noise removal processing as desired via the front panel 29.

The CPU 30 is a control unit configured to control the image processing apparatus 2, and, further, the whole endoscope system including the endoscope 1 and the light source apparatus 4. The endoscope system is configured so that a mode can be switched between the WLI mode in which observation is performed by irradiating the object with a white light and the NBI mode in which observation is performed by irradiating the object with a narrow band light, and the CPU 30 functions as a mode transitioning unit configured to make the mode transition from one mode to the other based on operation input from the front panel 29. The CPU 30 controls the periodic noise detecting unit 31, the brightness detecting unit 32, the NBI matrix processing unit 33, the smoothing processing unit 34 and the image enhancement processing unit 35 based on the periodic noise information obtained from the ROM 16 and performs various kinds of processing including processing of reducing periodic noise.

The periodic noise detecting unit 31 detects periodic noise in the image obtained from the image pickup device 15. Here, in the detection of the periodic noise, for example, judgement as to whether or not a luminance level difference between a pixel of interest and pixels horizontally or vertically adjacent to the pixel of interest is equal to or greater than a predetermined threshold is performed on, for example, ten successive pixels, and periodicity is judged from the result. However, the detection of the periodic noise is not limited to this example, and it is possible to apply other various kinds of techniques. The periodic noise detected by the periodic noise detecting unit 31 is compared with the periodic noise information read out from the ROM 16 by the CPU 30.

The brightness detecting unit 32 detects brightness of the image.

The NBI matrix processing unit 33 performs matrix operation processing of the image obtained in the NBI mode.

The smoothing processing unit 34 performs processing of smoothing the image to reduce noise noticeable in a flat portion of the image. Here, the smoothing processing is performed by, for example, detecting a luminance level of neighboring pixels (for example, pixels at a right side and a left side or pixels above or below) of a noise pixel, calculating a luminance average of the neighboring pixels to obtain a correction value, and replacing a pixel value of the noise pixel with the correction value. However, the smoothing processing is not limited to this example, and it is possible to apply other various kinds of techniques.

The image enhancement processing unit 35 performs processing of performing enhancement processing on the image to make contour and an edge of an image sharper.

The light source apparatus 4 is a light source unit including a WLI light source 4a configured to emit a white light (WLI light), and an NBI light source 4b configured to emit a narrow band light (NBI light).

Figure 10:
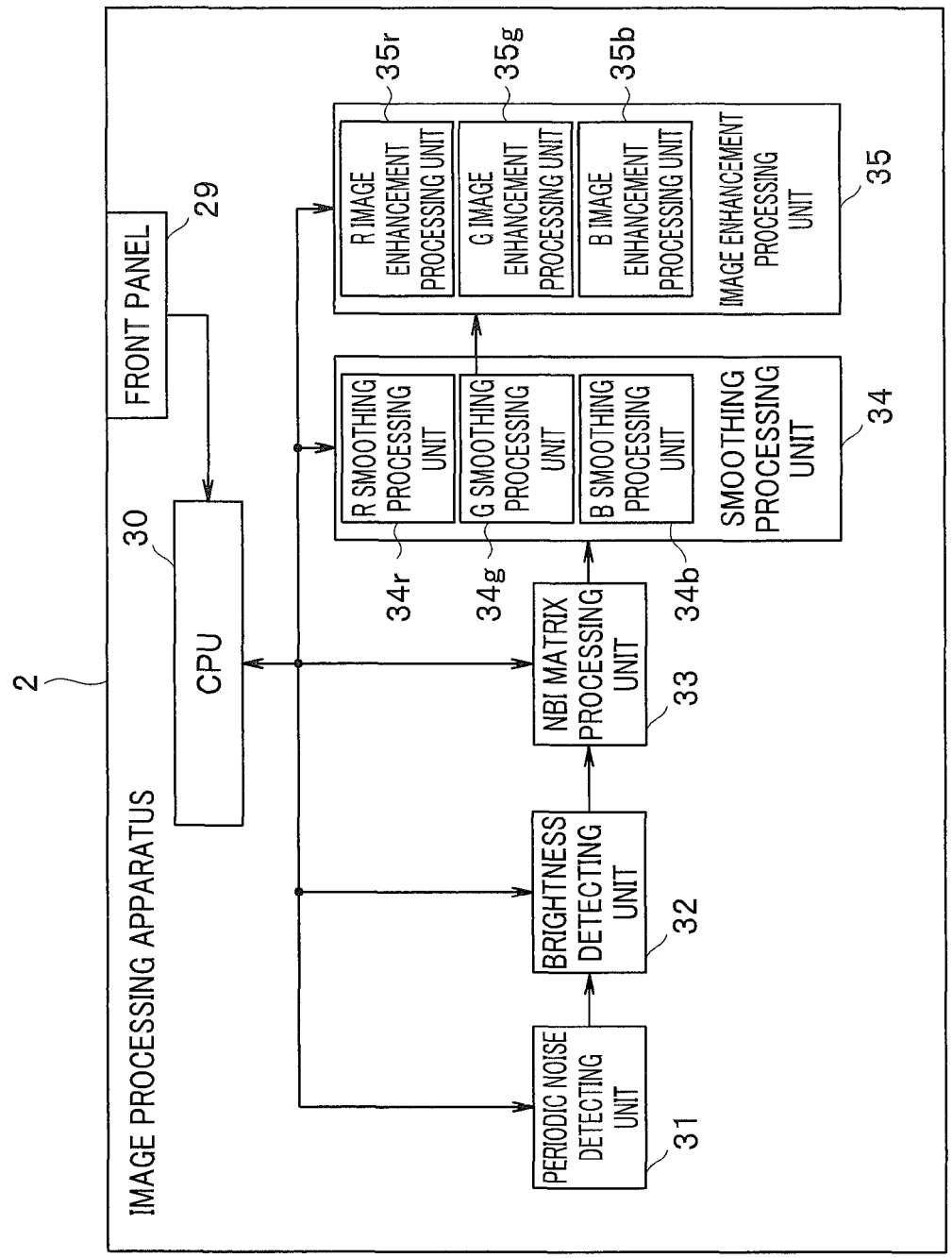
FIG. 10 is a block diagram illustrating details of a configuration of an image processing apparatus according to the above-described embodiments.

FIG. 10 is a block diagram illustrating details of the configuration of the image processing apparatus 2.

The smoothing processing unit 34, more specifically, includes an R smoothing processing unit 34r configured to smooth an image of an R (red) component, a G smoothing processing unit 34g configured to smooth an image of a G (green) component, and a B smoothing processing unit 34b configured to smooth an image of a B (blue) component, among color components constituting the image.

Also, the image enhancement processing unit 35, more specifically, includes an R image enhancement processing unit 35r configured to enhance an image of an R component, a G image enhancement processing unit 35g configured to enhance an image of a G component, and a B image enhancement processing unit 35b configured to enhance an image of a B component, among color components constituting the image.

Figure 11:
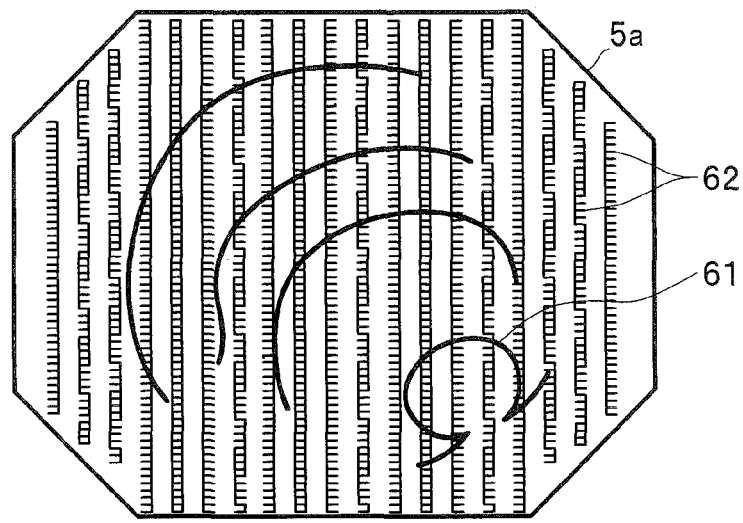
FIG. 11 is a diagram illustrating an example of periodic noise in an image according to the above-described embodiments.
Figure 12:
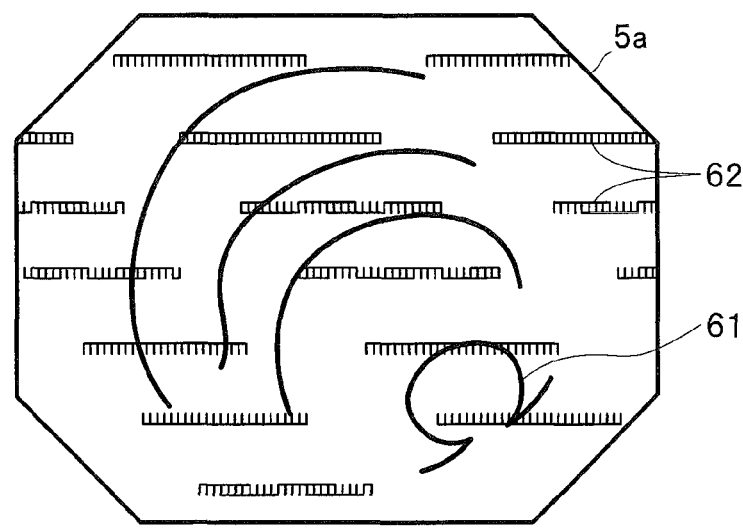
FIG. 12 is a diagram illustrating another example of the periodic noise in the image according to the above-described embodiments.

Next, FIG. 11 is a diagram illustrating one example of periodic noise in the image, and FIG. 12 is a diagram illustrating another example of the periodic noise in the image.

In FIG. 11 and FIG. 12, on a screen 5a of the monitor, an endoscope image 61 of the object is displayed, and periodic noise 62 is displayed.

Here, in the example illustrated in FIG. 11, the periodic noise 62 has a vertical stripe pattern having a fixed space interval in a horizontal direction.

Further, in the example illustrated in FIG. 12, the periodic noise 62 has a line-segment like horizontal stripe pattern having a fixed space interval in an oblique direction from an upper left part toward a lower right part.

Note that other examples of the periodic noise can include an oblique stripe pattern and a dot pattern.

Figure 13:
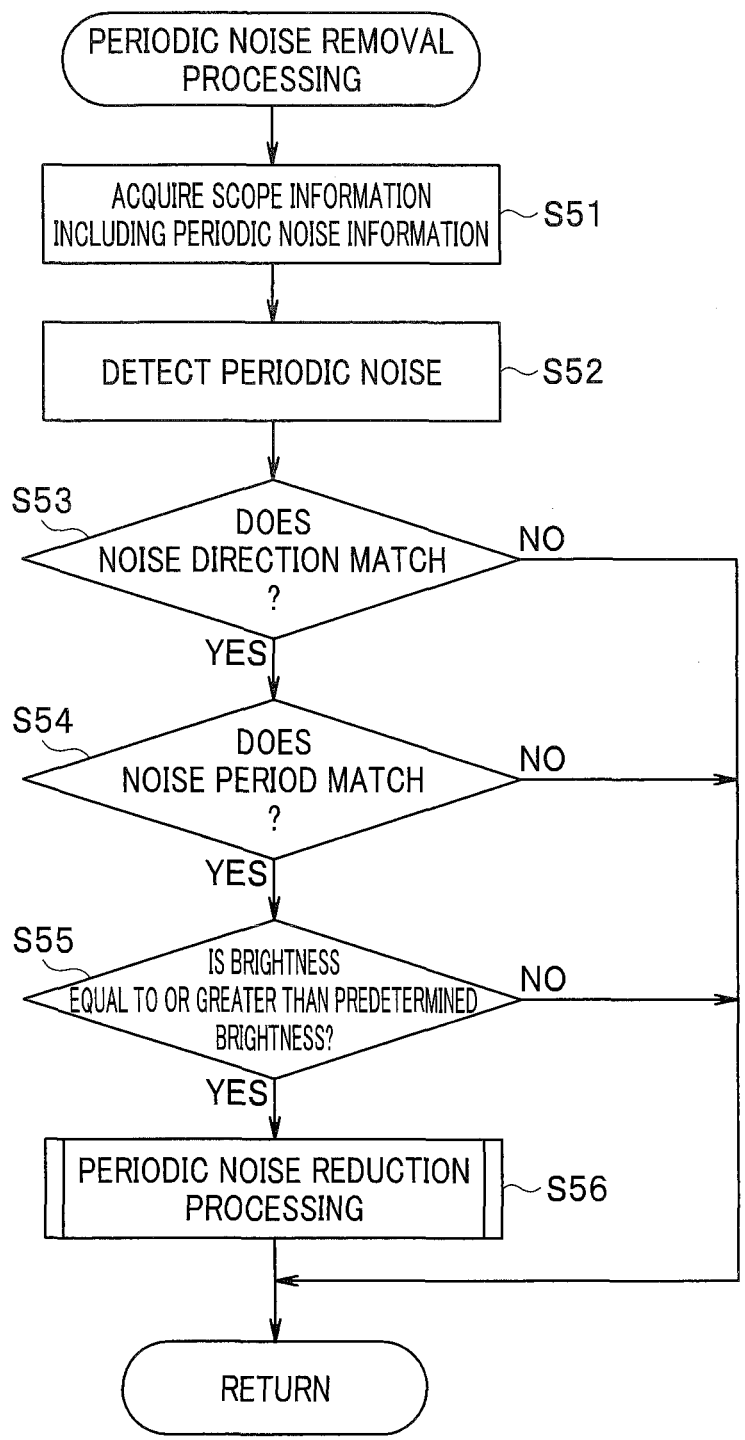
FIG. 13 is a flowchart illustrating a periodic noise removal processing in the endoscope system according to the above-described embodiments.

Subsequently, FIG. 13 is a flowchart illustrating a periodic noise removal processing in the endoscope system.

When the processing is called from the main processing, or the like, which is not illustrated, and execution of the processing is started, the CPU 30 acquires scope information including periodic noise information from the ROM 16 (step S51).

Further, the periodic noise detecting unit 31 detects periodic noise of the image acquired by the image pickup device 15 (step S52).

Then, the CPU 30 judges whether or not a noise direction of the periodic noise detected in step S52 matches a noise direction obtained from the periodic noise information acquired in step S51 (step S53).

When it is judged that the noise direction of the periodic noise matches the noise direction obtained from the periodic noise information, the CPU 30 further judges whether or not a noise period of the periodic noise detected in step S52 matches a noise period obtained from the periodic noise information acquired in step S51 (step S54).

When it is judged that the noise period of the periodic noise matches the noise period of the periodic noise information, the CPU 30 judges whether or not the brightness of the image obtained by the brightness detecting unit 32 is equal to or greater than predetermined brightness (step S55).

Figure 14:
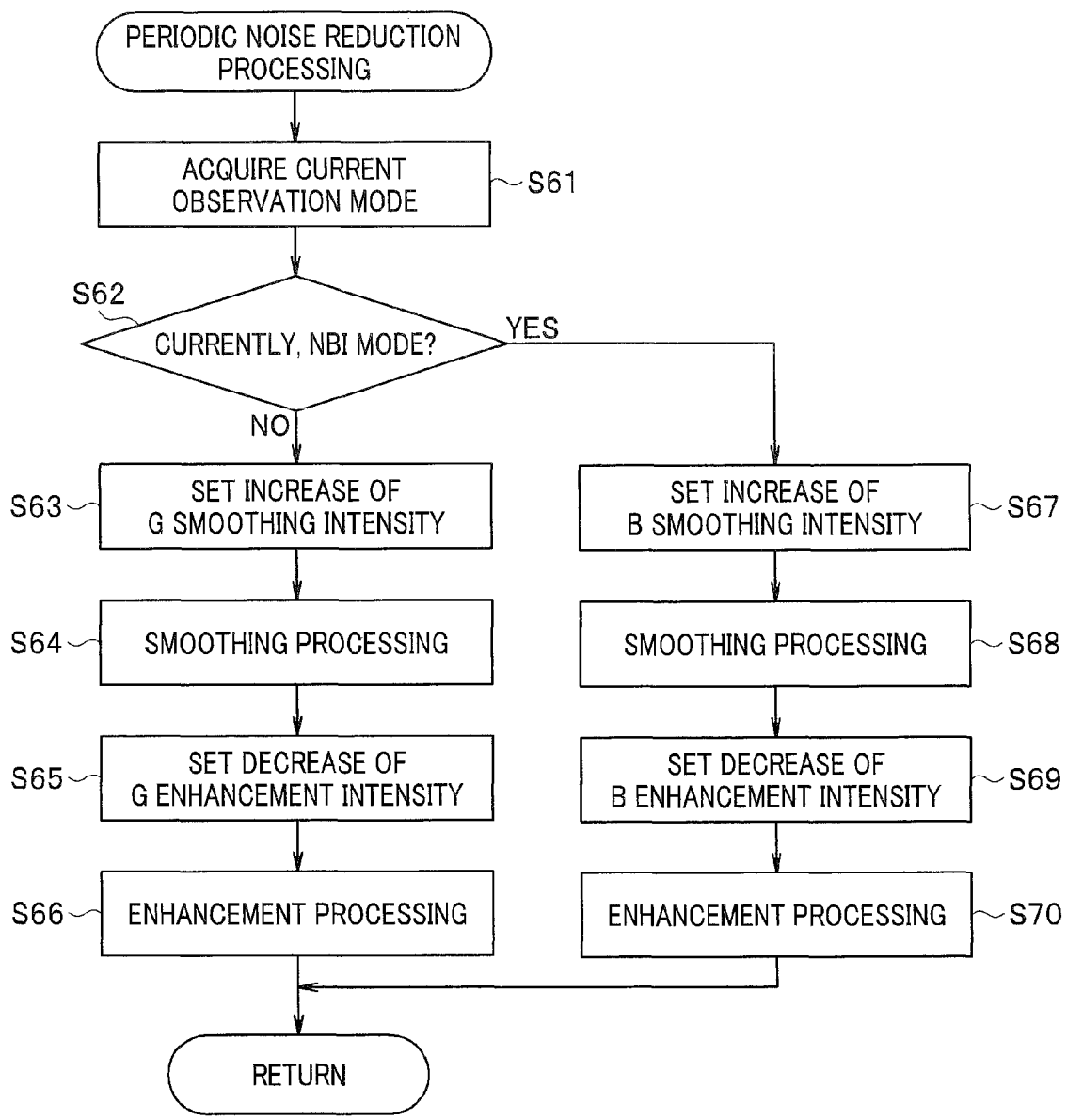
FIG. 14 is a flowchart illustrating details of a periodic noise reduction processing in step S56 in FIG. 13 according to the above-described embodiments.

When it is judged that the brightness of the image is equal to or greater than the predetermined brightness, periodic noise reduction processing is performed as illustrated in FIG. 14 which will be described later (step S56).

When the processing in step S56 is finished or it is judged that the noise direction of the periodic noise does not match the noise direction obtained from the periodic noise information in step S53, when it is judged that the noise period of the periodic noise does not match the noise period of the periodic noise information in step S54, or when it is judged that brightness of the image is not equal to or greater than the predetermined brightness in step S55, the processing is returned to the main processing which is not illustrated.

While, in the periodic noise reduction processing in step S56, as will be described later, intensity of enhancement processing is reduced by increasing intensity of smoothing processing, such processing can reduce periodic noise, but somewhat degrades image quality of the image. Therefore, to avoid unnecessary image processing, judgment processing in steps S53 to S55 is performed. That is, when both of the conditions in step S53 and step S54 are not satisfied, it is judged that the noise is not periodic noise, and the processing of step S56 is skipped. Further, while the periodic noise is noticeable in a bright portion of the image, the periodic noise is relatively not noticeable in a dark portion. Therefore, judgement in step S55 is performed, so that the processing of step S56 is performed only in a bright portion of the image.

Therefore, while the processing in FIG. 13 (and FIG. 14) may be performed in units of images, it is preferable to perform the processing in units of pixels of interest (or in units of blocks of pixels of interest, or the like) to avoid unnecessary periodic noise reduction processing.

FIG. 14 is a flowchart illustrating details of the periodic noise reduction processing in step S56 in FIG. 13.

When the processing is started, the CPU 30 acquires a current observation mode (step S61).

Then, the CPU 30 judges whether or not the current observation mode is the NBI mode (step S62).

Here, when it is judged that the current observation mode is not the NBI mode, but the WLI mode, the CPU 30 performs setting so as to increase smoothing intensity by the G smoothing processing unit 34g (that is, flatten the image) (step S63). Here, the periodic noise is noticeable in a signal where a level is high (for example, a bright portion of the image). Therefore, in order to make a noise component less noticeable in smoothing processing in a posterior stage, in an anterior stage of the smoothing processing, only smoothing intensity of a G component which is the highest level among the RGB components is set higher. Note that, taking into account a case where the object is a living body, smoothing intensity of an R component which is a main color component of blood vessels is not changed.

Subsequently, smoothing processing by the smoothing processing unit 34 is performed (step S64).

Further, the CPU 30 performs setting so as to decrease intensity of image enhancement by the G image enhancement processing unit 35g (step S65). Here, because the noise component is also enhanced by the enhancement processing in a posterior stage, in an anterior stage of the enhancement processing, only intensity of image enhancement of the G component which is the highest level among the RGB components is set lower. Note that, taking into account a case where the object is a living body, intensity of image enhancement for the R component which is the main color component of blood vessels is not changed.

Then, image enhancement processing by the image enhancement processing unit 35 is performed (step S66).

On the other hand, when it is judged that the current observation mode is the NBI mode in step S62, the CPU 30 performs setting so as to increase smoothing intensity by the B smoothing processing unit 34b (step S67).

Here, there is a case where efficiency of light incidence to the image pickup device 15 and light conversion efficiency at the image pickup device 15 vary depending on a wavelength of the light. For example, the way how the periodic noise appears is different between the white light (WLI light) and the narrow band light (NBI light), because a wavelength band is different. Particularly, in the NBI light, the periodic noise is more likely to appear in a B component which has a short wavelength than in a G component. Therefore, when the observation mode is the NBI mode, only smoothing intensity of the B component among the RGB components is set higher so as to efficiently reduce periodic noise while minimizing degradation of the image.

Subsequently, smoothing processing by the smoothing processing unit 34 is performed (step S68).

Further, the CPU 30 performs setting so as to decrease intensity of image enhancement by the B image enhancement processing unit 35b (step S69). Also here, for the same reason as described above in step S67, when the observation mode is the NBI mode, only intensity of image enhancement of a B component among the RGB components is set lower so as to efficiently reduce periodic noise while minimizing degradation of the image.

Then, image enhancement processing by the image enhancement processing unit 35 is performed (step S70).

When the processing in step S66 or step S70 is performed in this manner, the processing is returned.

According to the configuration as explained with reference to FIG. 9 to FIG. 14, it is possible to automatically select appropriate processing for periodic noise resulting from the image pickup device 15 according to observation modes and noise occurrence states and reduce noise while minimizing image degradation by image processing.

By the way, the endoscope includes a freeze switch for displaying a still image, and, when it is desired to observe a still image during observation of a moving image, a freeze instruction signal is generated by an operator operating the freeze switch, and a still image at the time when the signal is generated is displayed.

At this time, if the still image at the time when the freeze instruction signal is generated is displayed as is, if the acquired still image includes image blurring, the blurred image is displayed. Therefore, in order to minimize blurring of the still image to be displayed, a function of pre-freeze is proposed.

In the pre-freeze, first, a frame image obtained by the endoscope picking up a moving image of the object is associated with blurring amount information upon acquisition of the image, and images corresponding to the latest plurality of frames are always accumulated in a memory. Then, when a freeze instruction signal is generated, a frame image with the smallest blurring amount (minimum blurring image) is searched from the plurality of frame images accumulated in the memory using the freeze instruction signal as a trigger, and a frame image obtained through search is selected and displayed as a still image.

Further, in this pre-freeze function, a technique is proposed which enables the operator to set a desired pre-freeze level. Here, the pre-freeze level indicates how old image from a time point when the freeze instruction signal is generated should be set as a target of search of an image to be displayed as a still image, and, specifically, indicates how many frames the image should go back from the latest frame image to be set as a target of search.

When such a pre-freeze function is used, if the observation mode is switched, there is a case where the freeze image is disordered. This will be described with reference to FIG. 15 and FIG. 16.

Figure 15:
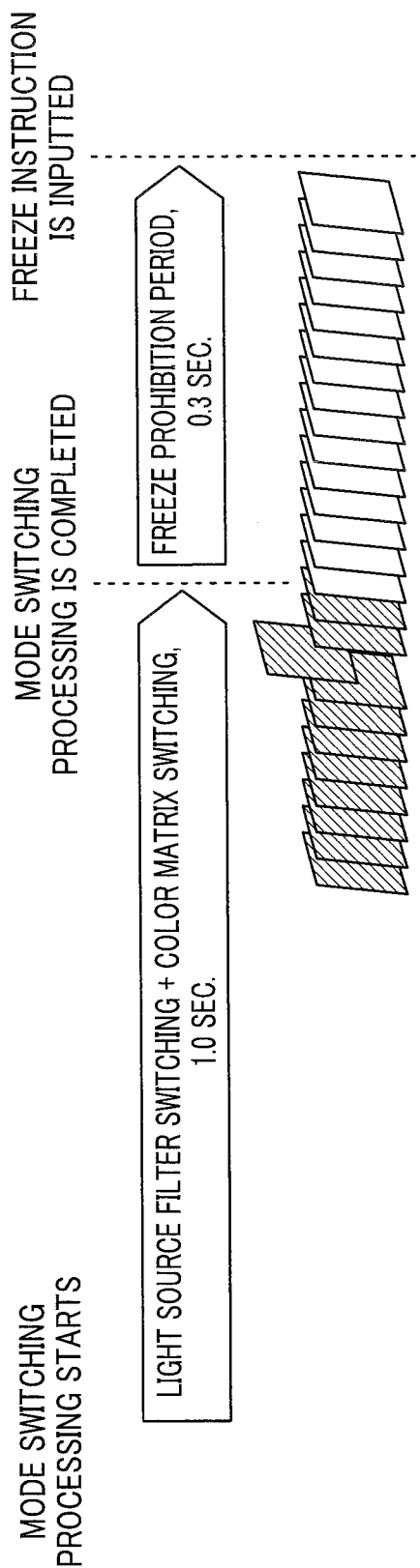
FIG. 15 is a timing chart for explaining disorder occurring in a freeze image after an observation mode is switched when a pre-freeze function is used according to the above-described embodiments.
Figure 16:
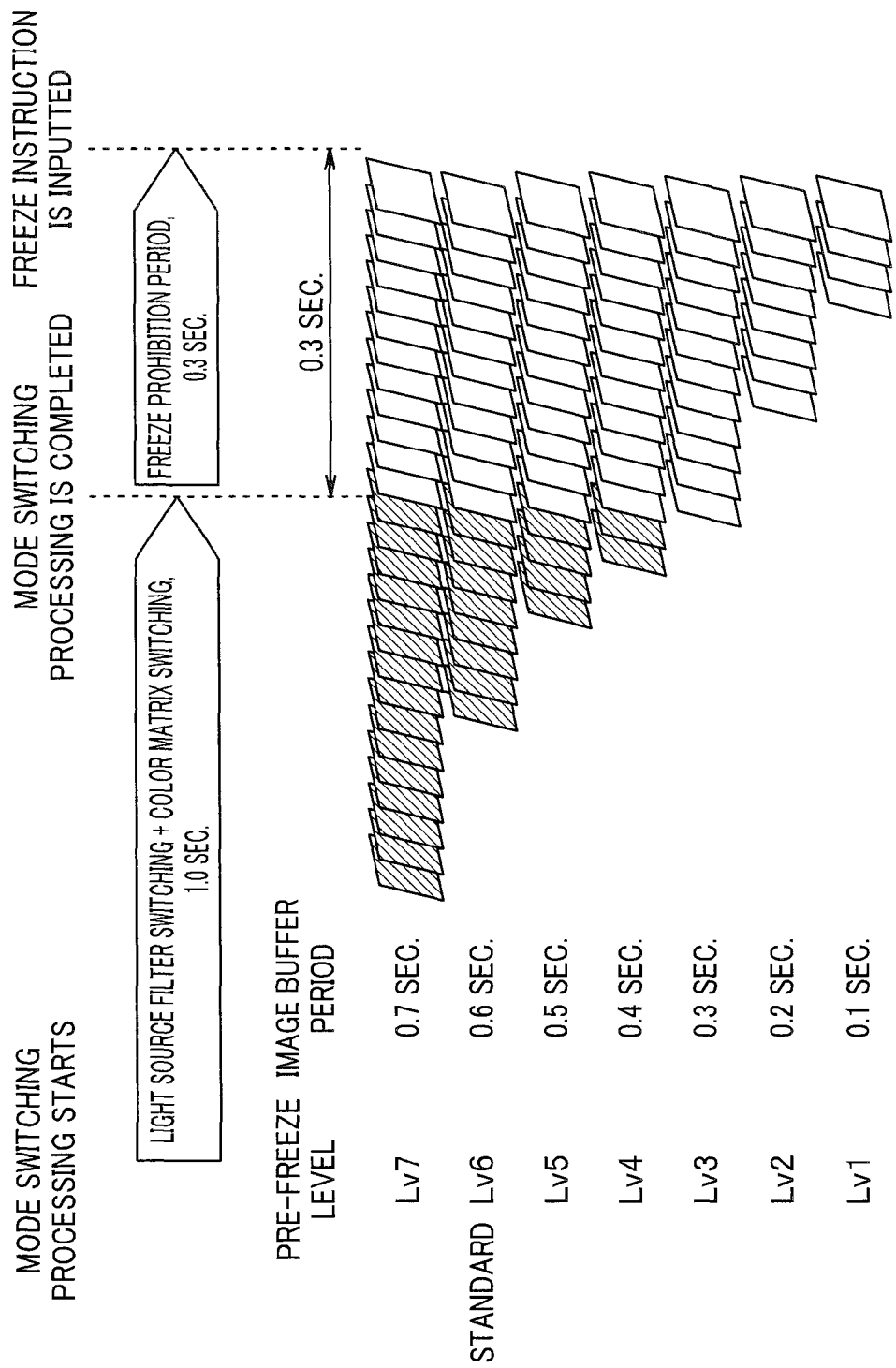
FIG. 16 is a timing chart for explaining aspect where whether or not disorder occurs in the freeze image after the observation mode is switched changes according to a pre-freeze level according to the above-described embodiments.

FIG. 15 is a timing chart for explaining disorder occurring in the freeze image after the observation mode is switched when the pre-freeze function is used, and FIG. 16 is a timing chart for explaining aspect where whether or not disorder occurs in the freeze image after the observation mode is switched, which is changing according to the pre-freeze level. Note that in FIG. 15, FIG. 16 and FIG. 17 which will be described later, each of a plurality of arranged rectangles indicates one frame image.

If freeze operation is performed when the observation mode is switched from any one of the observation modes among a plurality of observation modes including the WLI mode, the NBI mode, an AFI mode (auto-fluorescence observation mode), or the like, to any another observation mode, there is a possibility that one (in FIG. 15, for example, a hatched frame image illustrated by being moved slightly upward) of frame images acquired during switching of the mode (hatched frame images in FIG. 15 to FIG. 17) is selected as a minimum blurring image by the above-described pre-freeze function, and a still image whose color and luminance are disordered is displayed.

Therefore, during a period while a series of processing for switching the observation mode is executed, and a predetermined period (hereinafter, referred to as a freeze prohibition period) after the series of processing for switching the observation mode is completed, even if freeze operation by the freeze switch is performed, it is possible to design that the generated freeze instruction signal may not be accepted.

Specifically, as illustrated in FIG. 15, it is assumed that it takes, for example, 1.0 second to complete the processing for switching the observation mode, including start of processing for switching the observation mode, switching of a filter within the light source apparatus, switching of a color matrix used for matrix operation of image processing, or the like. At this time, it is possible to set, for example, 0.3 second after the processing for switching the observation mode is completed as the freeze prohibition period.

However, when the pre-freeze level can be set, there is a case where images searched by going back by longer than 0.3 second are set as a target of search, in which case, as illustrated in FIG. 15, a frame image acquired during execution of the processing for switching the observation mode can be selected as the minimum blurring image.

As illustrated in FIG. 16, it is assumed that the pre-freeze level can be set, for example, from level 1 (Lv1) to level 7 (Lv7), and a time length (image buffer period) of going back to search images to be set as a target of search in each level is set at 0.1 second for level 1 (Lv1), 0.2 second for level 2 (Lv2), 0.3 second for level 3 (Lv3), 0.4 second for level 4 (Lv4), 0.5 second for level 5 (Lv5), 0.6 second for level 6 (Lv6), and 0.7 second for level 7 (Lv7). Note that it is assumed that, among these levels, a level set as standard when no setting is performed by the operator is, for example, 0.6 second for level 6 (Lv6).

In this case, in the case of the freeze prohibition period of 0.3 second, while image disorder does not occur from level 1 (Lv1) to level 3 (Lv3), because frame images acquired during execution of the processing for switching the observation mode are included in the target of search when the level is from level 4 (Lv4) to level 7 (Lv7), there is a possibility that image disorder occurs. Particularly, because, if the pre-freeze level is higher, the frame images acquired during execution of the processing for switching the observation mode account for a larger portion of all the frame images which are the target of search, a possibility that image disorder occurs becomes further higher.

On the other hand, while it is possible to set the longest time period which can be set in the pre-freeze level, in the specific example illustrated in FIG. 16, 0.7 second for level 7 (Lv7) as a time length of the freeze prohibition period, in this case, because a time period during which freeze operation cannot be performed becomes longer, usability may degrade.

Figure 17:
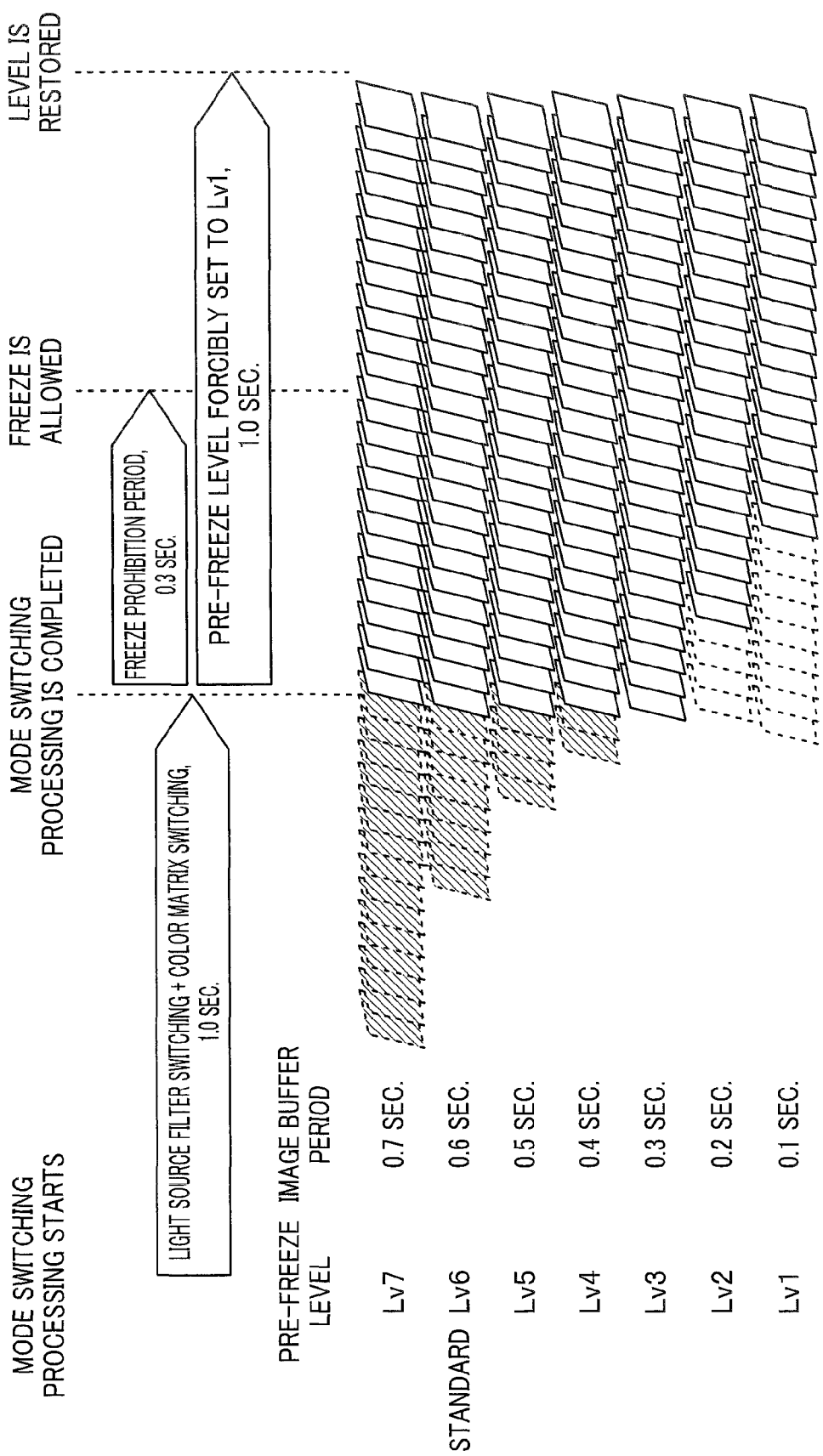
FIG. 17 is a timing chart illustrating aspect of control for preventing occurrence of disorder in the freeze image after the observation mode is switched according to the above-described embodiments.

Therefore, a technique for displaying a freeze image with small disorder while preventing degradation of usability will be described with reference to FIG. 17 and FIG. 18. Here, FIG. 17 is a timing chart illustrating aspect of control for preventing occurrence of disorder in the freeze image after the observation mode is switched, and FIG. 18 is a flowchart illustrating pre-freeze control processing for preventing occurrence of disorder in the freeze image after the observation mode is switched.

Figure 18:
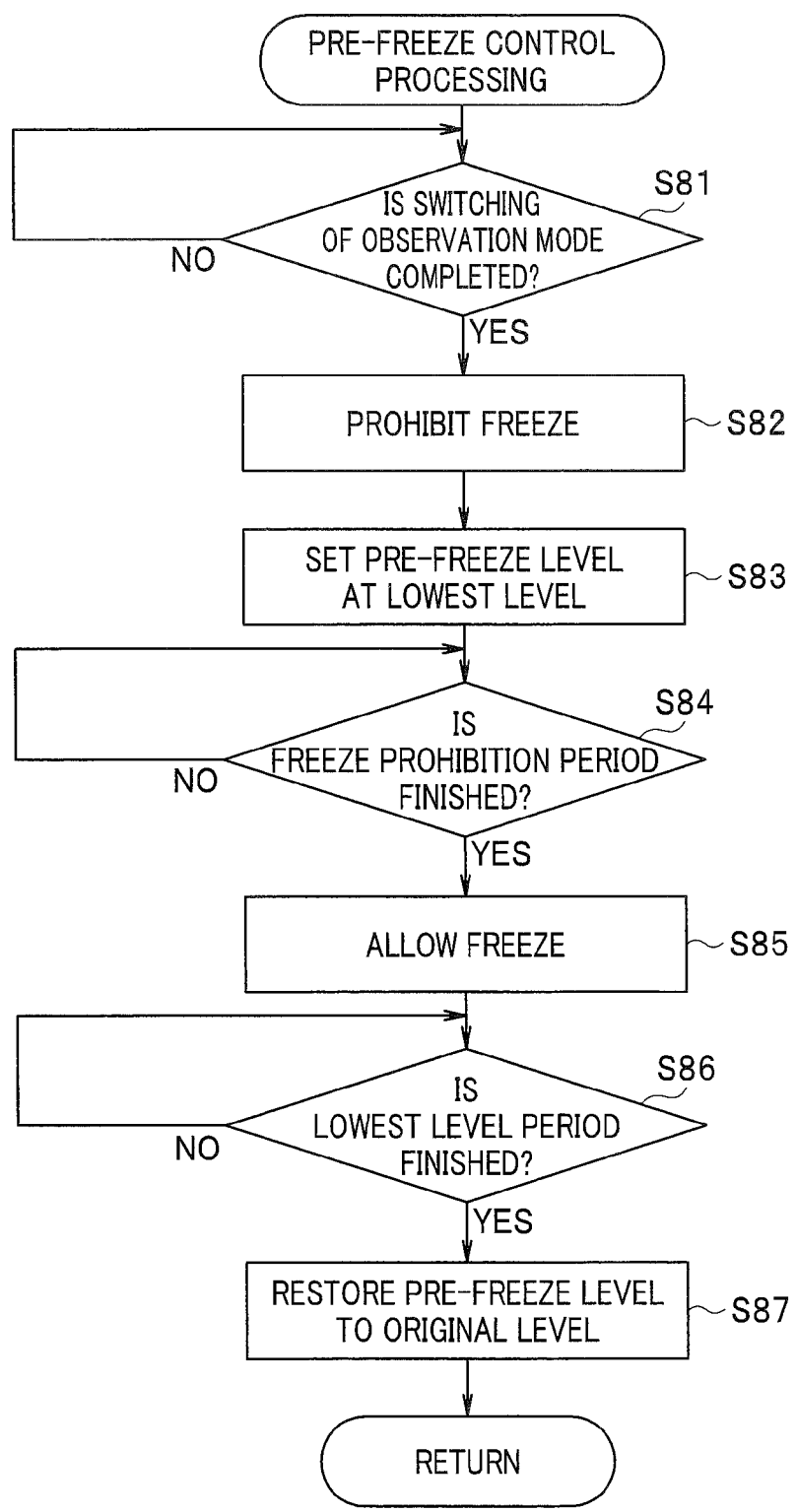
FIG. 18 is a flowchart illustrating a pre-freeze control processing for preventing occurrence of disorder in the freeze image after the observation mode is switched according to the above-described embodiments.

When the processing illustrated in FIG. 18 is started, first, it is waited until the processing for switching the observation mode is completed (step S81).

Then, after the processing for switching the observation mode is completed, the processing enters a freeze prohibition period during which acceptance of the freeze instruction signal is prohibited (step S82).

Further, the pre-freeze level is forcibly set at the lowest level, in a specific example, set at 0.1 second for level 1 (Lv1) (step S83).

Subsequently, it is waited until the freeze prohibition period (0.3 second in the example illustrated in FIG. 17) is finished (step S84).

Here, after the freeze prohibition period is finished, the freeze prohibition period is finished so that acceptance of the freeze instruction signal is allowed (step S85).

By this means, even if freeze operation is performed immediately after the freeze prohibition period is finished, because images going back by a time length of 0.3 second, which is the freeze prohibition period, from a time point at which the operation is performed, do not include disorder, and the image buffer period is 0.1 second, it is possible to prevent images with disorder from being set as a search target, so that it is possible to prevent disorder of a still image from being displayed.

Subsequently, it is waited until a lowest level period which is a time period during which the pre-freeze level is forcibly set at the lowest level is finished (step S86). The lowest level period is 1.0 second in the example illustrated in FIG. 17.

When the lowest level period is finished in this manner, the freeze level is returned to the previous level before the lowest level is set in step S83 (step S87), and the processing is returned from this processing.

Note that while the freeze prohibition period is set at 0.3 second in the example illustrated in FIG. 17, when the level 1 (Lv1) which is the lowest level in the pre-freeze is 0.1 second, the freeze prohibition period may be 0.1 second or longer. More generally, if the freeze prohibition period is T0, and the image buffer period of the lowest level in the pre-freeze is T1, the freeze prohibition period may be set at any period if $T0 \geq T1$. At this time, by setting the freeze prohibition period T0 so as to be equal to T1 (for example, 0.1 second), it is possible to further improve usability while minimizing the freeze prohibition period.

Alternatively, if the freeze prohibition period is set at 0.3 second, instead of the level forcibly set in step S83 being level 1 (Lv1) which is the lowest level, it is also possible to set level 2 (Lv2) or level 3 (Lv3) which is longer than the image buffer period (that is, it is more likely to find an image with a smaller blurring amount).

Further, while the lowest level period is set at 1.0 second in the example illustrated in FIG. 17, when level 7 (Lv7) which is the highest level in the pre-freeze is, for example, 0.7 second, the freeze prohibition period T0 may be set at 0.7 second or longer. More generally, when the image buffer period of the highest level in the pre-freeze is TL, the freeze prohibition period may be set at any period if $T0 \geq TL$. By this means, even if the original pre-freeze level is any level, it is possible to prevent disorder of the still image to be displayed through freeze operation after the level is restored.

In addition, when the image buffer period corresponding to the freeze level is Tx, an elapsed time period since the processing for switching the observation mode is completed is t, and the image buffer period of the original pre-freeze level is Tb, it is possible to dynamically change the image buffer period Tx as Tx=t during a period of 0<t<Tb, and restore the level to Tx=Tb from a time point when t=Tb. In this case, it is not only possible to prevent disorder of the still image to be displayed, but also possible to set a period during which freeze is prohibited to substantially 0, and further it is possible to search a minimum blurring image from all the frame images with no disorder acquired after the processing for switching the observation mode is completed during a period of 0<t<Tb, so that it is possible to provide an advantage that a still image with smaller blurring can be observed.

According to the configuration as described with reference to FIG. 15 to FIG. 18, even if the observation mode is switched under conditions that the pre-freeze function is set, it is possible to display a freeze image with small disorder while preventing degradation of usability.

Note that, while the image pickup apparatus has been mainly described above, the above description may be applied to an operation method of the image pickup apparatus, a processing program for causing a computer to execute the operation method of the image pickup apparatus, a non-transitory computer readable recording medium recording the processing program, or the like.

Further, the present invention is not limited to the above-described embodiments as is, and can be embodied by modifying components without deviating from the spirit in an implementation stage. Further, various aspects of the invention can be made by combining a plurality of components disclosed in the above-described embodiments as appropriate. For example, it is also possible to delete some components from all the components described in the embodiments. Still further, it is also possible to combine components over different embodiments as appropriate. In this manner, it is of course possible to make various modifications and application without departing from the spirit of the invention.

What is claimed is:
1. An image pickup apparatus comprising:
   a light source configured to emit a first illumination light having a first light emission amount or a second illumination light having a second light emission amount to an object, wherein the second light emission amount is smaller than the first light emission amount;

an image sensor configured to pick up an image of the object illuminated with the first illumination light or the second illumination light; and a processor comprising hardware, wherein the processor is configured to:

switch a mode from one of a first mode in which the image is picked up by illuminating the object with the first illumination light and a second mode in which the image is picked up by illuminating the object with the second illumination light, to the other mode; and set a processing parameter for processing the image picked up by the image sensor in a mode after the mode is switched, wherein when the mode is switched from the first mode to the second mode, the processor is configured to set the processing parameter in the second mode after switching of the illumination light from the light source to an illumination light corresponding to the second mode is completed to make color disorder of the image less noticeable, and wherein when the mode is switched from the second mode to the first mode, the processor is configured to set the processing parameter in the first mode before switching of the illumination light from the light source to an illumination light corresponding to the first mode is started to make color disorder of the image less noticeable.

2. The image pickup apparatus according to claim 1, wherein the processor is configured to:

set a brightness control parameter for controlling intensity of the illumination light emitted from the light source before the illumination light emitted from the light source is switched to an illumination light corresponding to the mode after the mode is switched or after switching to the illumination light corresponding to the mode after the mode is switched is completed; and calculate brightness of the image picked up by the image sensor, and wherein the brightness control parameter is a parameter for setting a frequency to calculate the brightness.

3. The image pickup apparatus according to claim 2, wherein the processor is configured to set the brightness control parameter so that the calculation frequency is higher within a predetermined time period after switching of the mode is completed than calculation frequency before the mode switches.

4. The image pickup apparatus according to claim 1, wherein the processor is configured to:

set a brightness control parameter for controlling intensity of the illumination light emitted from the light source before the illumination light emitted from the light source is switched to an illumination light corresponding to the mode after the mode is switched or after switching to the illumination light corresponding to the mode after the mode is switched is completed; and set the brightness control parameter in units of a changing step, and set a larger changing step within a predetermined time period immediately after switching of the mode is completed than the changing step at a normal time.

5. An operation method of an image pickup apparatus, the operation method comprising:

an illumination step of a light source unit emitting a first illumination light having a first light emission amount or a second illumination light having a second light emission amount to an object, wherein second light emission amount is smaller than the first light emission amount;

an image picking up step of an image sensor picking up an image of the object illuminated with the first illumination light or the second illumination light;

a mode switching step of a processor comprising hardware switching a mode from one of a first mode in which the image is picked up by illuminating the object with the first illumination light and a second mode in which the image is picked up by illuminating the object with the second illumination light, to the other mode; and a parameter setting step of the processor setting a processing parameter for processing the image picked up in the image acquiring step in a mode after the mode is switched, wherein when the mode is switched from the first mode to the second mode, the parameter setting step comprises setting the processing parameter in the second mode after switching of the illumination light from the light source to an illumination light corresponding to the second mode is completed to make color disorder of the image less noticeable, and wherein when the mode is switched from the second mode to the first mode, the parameter setting step comprises setting the processing parameter in the first mode before switching of the illumination light from the light source to an illumination light corresponding to the first mode is started to make color disorder of the image less noticeable.

* * * * *